US00PP13376P2

(12) United States Plant Patent
Matoba

(10) Patent No.: US PP13,376 P2
(45) Date of Patent: Dec. 17, 2002

(54) PLUM TREE NAMED 'SUNLITE NUGGET'

(76) Inventor: Frank T. Matoba, 8098 E. American Ave., Del Rey, CA (US) 93616-9722

( * ) Notice: Subject to any disclaimer, the term of this patent is extended or adjusted under 35 U.S.C. 154(b) by 0 days.

(21) Appl. No.: 09/578,459

(22) Filed: May 20, 2000

(51) Int. Cl.[7] ..... A01H 5/00
(52) U.S. Cl. ..... Plt./184
(58) Field of Search ..... Plt./184

(56) References Cited

U.S. PATENT DOCUMENTS

PP2,674 P * 7/1965 Campagne ..... Plt./184
PP9,162 P * 6/1995 Zaiger et al. ..... Plt./184

* cited by examiner

*Primary Examiner*—Bruce R. Campell
*Assistant Examiner*—W C Baker
(74) *Attorney, Agent, or Firm*—Worrel & Worrel

(57) ABSTRACT

A new and distinct variety of plum tree *Prunus Salicina* derived as an open pollinated hybrid from the 'Red Beaut' plum tree (U.S. Plant Pat. No. 2,539), but from which it is distinguished by producing fruit of high quality having a distinctive flavor, a generally green skin coloration and regular bearing, the variety developed as a hybridized seedling from the aforementioned selected seed parent and an unnamed seedling as the selected pollen parent.

1 Drawing Sheet

BACKGROUND OF THE NEW VARIETY

The present invention relates to a new and distinct variety of plum tree, *Prunus Salicina*, which will hereinafter be denominated varietally as the 'Sunlite Nugget' plum tree, and, more particularly, to a plum tree which produces early maturing fruit, which are mature for commercial harvesting and shipment approximately May 17 to May 24 in the San Joaquin Valley of central California, producing generally large, high quality fruit, having green skin coloration.

The discovery and development of new varieties of fruit, and particularly tree fruit, is an assiduous task requiring great effort, substantial botanical knowledge, an equivalent knowledge of the marketplace, a considerable amount of good fortune, and time testing. From the point of view of the marketplace, the maturation period and fruit characteristics are frequently all important. Similarly, such criteria as flavor, size, color and shipability are of significant importance, as well as a multitude of other factors bear upon the success of any new variety. Therefore, the new variety was selected for asexual reproduction and commercialization.

The new variety of the instant invention is a plum tree characterized by its bearing of fruit of early maturation, of comparatively large size, of high quality, of shipability and of productivity, both for local usage, as well as packing and shipment to distant markets. The fruit of the new variety has been stored for twenty-one (21) days at 32° to 34° Fahrenheit without adverse affect. The productivity of fruit per tree of the new variety has generally consisted of from 50.8 kg (112 pounds) to 63.5 kg (140 pounds) of mature fruit. In addition, the fruit of the instant variety is of a generally green coloration which has been in demand, but effectively unavailable in the marketplace. In fact, the maturation date of the new variety of the instant invention is similar to that of the 'Red Beaut' plum tree (U.S. Plant Pat. No. 2,539), but the fruit of which is of a generally green coloration, rather than a red coloration. The new and distinct variety is broadly characterized by a medium size, medium vigorous, hardy, productive, and regular beaing tree, which requires a pollinator such as the 'Santa Rosa' plum tree (unpatented). During the 2001 growing season, measurements were taken from the nineteen year old original tree of the new variety. The tree had a height of 5.18 m (17 feet) which included 1.83 m (6 feet) of new growth and a spread of 3.66 m (12 feet).

Therefore, the 'Sunlite Nugget' plum tree of the instant invention is believed to be a promising candidate to meet a need in the marketplace which has long been recognized.

ORIGIN AND ASEXUAL REPRODUCTION OF THE NEW VARIETY

The present variety of plum tree hereof was selected by the inventor in his orchard near Del Rey, in Fresno County, in the San Joaquin Valley of California. The new variety is an open pollinated seedling of the 'Red Beaut' plum tree (U.S. Plant Pat. No. 2,539). The inventor selected the newly found seedling from a test plot of approximately fifty (50) seedlings in May of 1980 near Del Rey, Calif. The new variety was asexually reproduced at the inventor's direction by budding and whip grafting in 1982 near Parlier, in Fresno County, in the San Joaquin Valley of California. The instant Variety was propagated on Nemaguard peach (unpatented) rootstock. The test location was to confirm that the same distinctive characteristics were found in the trees of the new variety grown under other soil and farming conditions. The progeny of the new variety have been observed and evaluated since that date. The asexually reproduced trees of the new variety observed since that date have been found to be identical in all respects to the parent tree including the fruit thereof.

SUMMARY OF THE NEW VARIETY

The 'Sunlite Nugget' plum tree is characterized by producing early maturing, high quality, large sized fruit which have a green skin coloration and are ripe for commercial harvesting and shipment approximately May 17 to May 24 in the San Joaquin Valley of central California. The new variety of plum tree of the instant invention may be compared to the 'Red Beaut' plum tree (U.S. Plant Pat. No. 2,539) with the early maturation of the fruit thereof, and including its high quality, productivity and green skin coloration.

BRIEF DESCRIPTION OF THE DRAWING

The accompanying drawing is a color photograph of mature fruit of the new variety showing a first in plan view showing the stem cavity thereof; a second sectioned along the suture and laid open to expose representative flesh coloration with the stone removed to expose the pit well of one section and the stone in place in the other section; a third in side elevation; a fourth in plan view showing the apex end thereof; a fifth in side elevation exposing the suture thereof; a stone of the new variety; and a portion of representative young growth and foliage.

DETAILED BOTANICAL DESCRIPTION

Referring more specifically to the botanical details of this new and distinct variety of plum tree, the following has been observed under the ecological conditions prevailing at the orchard of origin which is located near Del Rey, in Fresno County, in the San Joaquin Valley of California. All major color code designations are by reference to the *Dictionary of Color*, by Maerz and Paul, First Edition, 1930. Common color names are also occasionally employed.

TREE

Generally: Size — Normal for a plum tree, subject to pruning and other horticultural practices. The size, figure and shape of the instant variety of plum tree are approximately the same as the 'Red Beaut' plum tree (U.S. Plant Pat. No. 2,539).

*Vigor.*—Vigorous. Similar to the 'Red Beaut' plum tree (U.S. Plant Pat. No. 2,539).

*Form.*—Upright to upright-spreading. Height from 5.18 m (17 feet) total height including 1.83 m (6 feet) of new growth and a spread of 3.66 m (12 feet).

*Figure.*—Trained to a relatively open vase configuration.

*Productivity.*—Productive. From 50.8 kg (112 pounds) to 63.5 kg (140 pounds) per tree.

*Regularity of bearing.*—Regular and hardy under the conditions typically prevailing in the San Joaquin Valley of central California.

Trunk:

*Size.*—Relatively thick with moderate amounts of scarfskin present.

*Surface texture.*—Moderately coarse.

*Color.*—Varies from a grey-brown (8-E-9 Negro Brown) to a brown-grey (8-E-10 Seal Brown).

*Lenticels.*—Numbers — Numerous present throughout the bark surface.

*Lenticels.*—Size — Medium.

Branches:

*Size.*—Average thickness.

*Surface texture.*—Medium.

*Color.*—One year or older wood — Brown-grey (8-J-10 Falcon Brown).

*Color.*—Immature Branches — Medium green (23-L-3 Hellebore Green) with a reddish tinge of coloration on shoots exposed to direct sunlight.

*Immature shoot tips.*—Exhibit a rusty coloration (6-A-12 Rust) becoming more greenish and then fully green with advancing maturity.

Leaves:

*Size.*—Generally — Mature leaves are of medium size. Leaf measurements recorded have been taken from vigorous shoots of current season's growth and are in the largest size ranges.

*Average length.*—Varies from 12.5 cm (4.875 inches) to 14.0 cm (5.46 inches), including the petiole.

*Average width.*—Varies from 5.1 cm (1.989 inches) to 5.9 cm (2.301 inches). The leaf is moderately thick with a moderately rugose upper surface.

*Form.*—Variable, most frequently long and obovate, but at times the leaf form is nearly oval.

*Base.*—Cuneate in form.

*Apex.*—Acuminate and usually slightly twisted sideways.

*Color.*—Upwardly disposed surface — Dark green (24-C-9).

*Color.*—Downwardly disposed surface — Light grey-green (22-I-4).

*Marginal form.*—Generally — Crenate with medium sized and somewhat irregular crenations. Crenations are often doubly so. The leaf margins are only slightly undulate.

*Petiole.*—Size — Generally medium.

*Petiole.*—Length — Ranges from 13 mm (0.52 inches) to 16 mm (0.63 inches).

*Petiole.*—Thickness — Ranges from 1.5 mm (0.06 inches) to 2.0 mm (0.08 inches).

*Petiole.*—Color — Lower Surface — Light green (20-H-4).

*Bud scale.*—Surface — Substantially glabrous.

*Flower buds.*—Generally — Buds are generally free from the bearing branch. The buds are hardy under typical climatic conditions in the central San Joaquin Valley of California.

*Flower buds.*—Size — Medium.

*Flower buds.*—Form — Plump and conic.

*Date of bloom.*—February 23 in 1993. In comparison, the date of full bloom for the 'Santa Rosa' plum tree (unpatented) in this same area was February 27 in 1993. The 'Santa Rosa' plum tree (unpatented) is considered a mid-season blooming cultivar.

*Bloom timing.*—Early in relation to other commercial plum cultivars grown in this region.

*Bloom quantity.*—Abundance of bloom was variable on the tree in 1993. Some areas of the tree were average in bloom quantity while other areas were light to very light. In general, the bloom for 1993 was less than average. The number of flowers per node was quite variable, from 1 to as many as 6 could be present.

*Size.*—Generally — Medium to large.

*Flower.*—Size — Diameter — Fully opened flowers ranges from 17 mm (0.68 inches) to 21 mm (0.84 inches).

*Petals.*—Color — Uniform white (1-A-1).

*Petals.*—Size — Medium to large.

*Sepal.*—Surface — Glabrous.

*Sepal.*—Margins — Relatively smooth with only an occasional serration.

*Sepal.*—Margins — Color — Light rose (2-I-7).

*Anthers.*—Size — Generally average.

*Anther.*—Color — Variable. The dorsal side of the anthers is an orange red (3-J-11 Blaze Sheik) when young and slightly darker along the anther margins. The ventral side of the anthers is a lighter orange-yellow (10-K-9 Sunburst). Anther coloration becomes somewhat lighter with age both dorsally and ventrally.

*Pollen.*—Moderate in abundance.

*Pollen.*—Color — Yellow-gold (10-K-6 Chinese Yellow).

*Stamens.*—Size — Length — Variable from 5 mm (0.2 inches) to 9 mm (0.36 inches), including the ovary.

*Pistil.*—Color — Pale green (19-I-2).

FRUIT

Maturity when described: Ripe for commercial harvesting and shipment approximately May 17 to May 24 in 1992 near Del Rey and Parlier in Fresno County in the San Joaquin Valley of California.

Size:

*Generally.*—Large and uniform.

*Average diameter in the axial plane.*—Ranges from 54 mm (2.16 inches) to 56 mm (2.24 inches).

Stem:

*Size.*—Medium.

*Stem.*—Size — Length — Varies from 13 mm (0.52 inches) to 15 mm (0.60 inches).

*Stem.—Size — Thickness — Moderately thick, ranging from* 3.0 mm (0.12 inches) to 3.5 (0.14 inches).

*Stem.*—Color — Variable from a greenish-brown (14-J-3) to light brown (14-H-6).

*Apex.*—Shape — Somewhat raised, but rounded at the tip.

*Pistil point.*—Position — Somewhat variable, but is most often apical.

*Pistil point.*—Characterized by a callous spot.

*Base.*—Form — Variable from rounded to very slightly truncate.

*Base.*—Angle — Variable from very slightly oblique to nearly at right angle to the fruit axis.

Skin:

*Thickness.*—Average.

*Surface.*—Glabrous. The skin is moderately acidic and is tenacious to the flesh at commercial maturity. The skin is uniformly covered with a light grey bloom.

*Tendency to crack.*—No tendency to crack has been observed.

*Blush color.*—Red blush color occurs in a washed pattern, first at the apex and then along the ventral suture area. Percentage of blush increases from 10 percent to 25 percent at commercial maturity. Small dark green areas can be present at times over the surface of the fruit in random pattern and dark green (21-K-5 Biscay Green) striping can be present over the basal shoulders parallel to the suture. Blush color ranges from (3-G-3 Moss Rose) to (3-K-4 Claret Bordeaux).

*Ground color.*—At commercial maturity the fruit exhibits from 70 percent to 90 percent green (20-K-5 Verdant Green) ground color to 19-L-5 Cosse Green). Numerous light colored dots are present throughout the skin surface.

Flesh:

*Flesh color.*—Light yellow (9-K-2 Chrome Lemon) with an even lighter yellow (9-H-2) near the stone cavity. A moderate number of light colored medium length fibers are present throughout the flesh. Within the cavity itself the flesh is darker than the general flesh color (11-K-6 Rattan Yellow).

*Flavor.*—Sweet with moderate acidity. In general the flavor is well balanced and pleasant.

*Aroma.*—Slight and pleasant.

*Texture.*—Moderately firm, fine textured and juicy. An occlusion or small cavity often occurs at the pit apex within the fruit. Occasionally a smaller cavity is present at the base of the stone.

*Eating quality.*—Very good.

Having thus described and illustrated my new variety of plum tree, what I claim as new and desire to be secured by Plant Letters Patent is:

1. A new and distinct variety of plum tree substantially as illustrated and described which is somewhat similar to the "Red Beaut" plum tree (U.S. Plant Pat No. 2,539) and relative to ripening date, but from which it is well distinguished in numerous respects by producing fruit which are mature for commercial harvesting and shipment approximately May 17 to May 24, in the San Joaquin Valley of central California while having a generally green skin coloration and productivity as opposed to the fruit of the aforementioned plum variety.

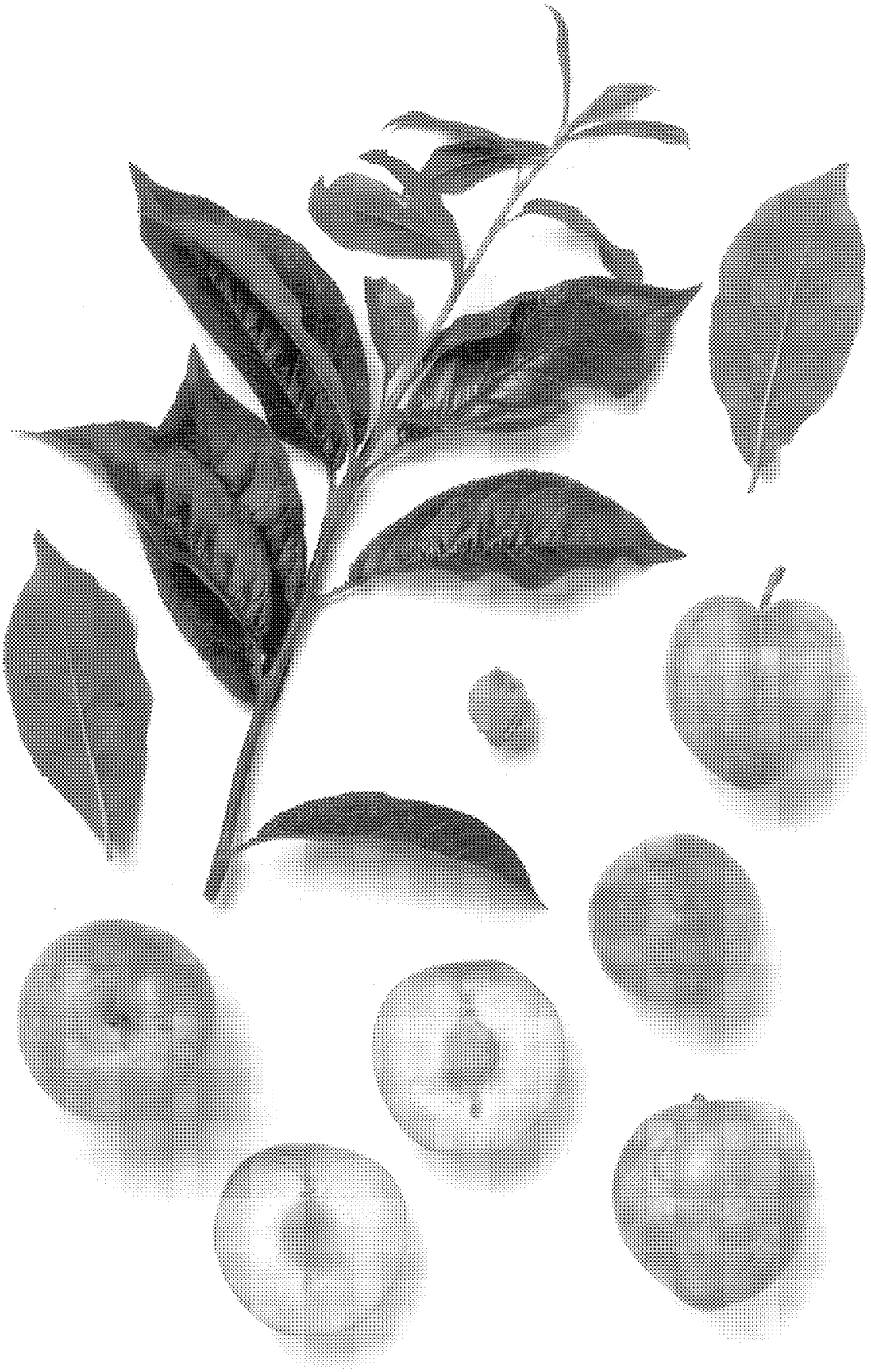

* * * * *